(12) United States Patent
Barnfield Frej et al.

(10) Patent No.: US 9,423,351 B2
(45) Date of Patent: Aug. 23, 2016

(54) SENSOR ATTACHMENT ARRANGEMENT FOR FLEXIBLE BAGS

(75) Inventors: Kine Barnfield Frej, Uppsala (SE); Owe Salven, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/515,820

(22) PCT Filed: Jun. 15, 2010

(86) PCT No.: PCT/SE2010/050668
§ 371 (c)(1),
(2), (4) Date: Jun. 14, 2012

(87) PCT Pub. No.: WO2011/075036
PCT Pub. Date: Jun. 23, 2011

(65) Prior Publication Data
US 2012/0291238 A1    Nov. 22, 2012

(30) Foreign Application Priority Data

Dec. 17, 2009  (SE) ...................................... 0950977

(51) Int. Cl.
*C12M 1/34*       (2006.01)
*C12M 3/00*       (2006.01)
(Continued)

(52) U.S. Cl.
CPC ............. *G01N 21/645* (2013.01); *C12M 23/00* (2013.01); *C12M 23/14* (2013.01); *C12M 27/16* (2013.01);
(Continued)

(58) Field of Classification Search
CPC .... C12M 1/34; C12M 1/3446; C12M 1/3453; C12M 23/40; C12M 23/26; C12M 23/14; C12M 41/12; C12M 41/26; C12M 23/00; B01L 3/00; B01L 3/563; G01N 21/645; G01N 2021/6484; G01N 2201/021; Y10T 24/45
USPC ....................................................... 435/288.7
See application file for complete search history.

(56) References Cited

U.S. PATENT DOCUMENTS 5,763,279 A * 6/1998 Schwarz et al. ........... 435/297.1
6,086,574 A   7/2000 Carroll et al.
(Continued)

FOREIGN PATENT DOCUMENTS

CN    1202246 A    12/1998
CN    1322254 A    11/2001
(Continued)

OTHER PUBLICATIONS

Search Report dated May 20, 2013 issued on corresponding Chinese patent application No. 201080057276.3.
(Continued)

*Primary Examiner* — Nathan Bowers
*Assistant Examiner* — Timothy Barlow
(74) *Attorney, Agent, or Firm* — Wood IP LLC

(57) ABSTRACT

An optical sensor holding device adapted to be integrated with a flexible bag, said device comprising a bag attachment part made from a material that can be welded to the flexible bag; a sensor attachment part made from a material to which an optical sensor spot can be attached, wherein the sensor attachment part is forced into an opening in the bag attachment part that is slightly smaller than the sensor attachment part such that the sensor attachment part is kept firmly in place and leakage is minimized.

8 Claims, 11 Drawing Sheets

(51) Int. Cl.
    *G01N 21/64* (2006.01)
    *C12M 1/00* (2006.01)
    *C12M 3/06* (2006.01)
(52) U.S. Cl.
    CPC ....... *C12M 41/00* (2013.01); *G01N 2021/6484* (2013.01); *G01N 2201/021* (2013.01); *Y10T 24/45* (2015.01)

(56) References Cited

U.S. PATENT DOCUMENTS

| | | | |
|---|---|---|---|
| 6,536,805 B2 * | 3/2003 | Matkovich | 285/3 |
| 6,815,211 B1 * | 11/2004 | Blazewicz et al. | 436/166 |
| 2005/0163667 A1 | 7/2005 | Krause | |
| 2006/0240546 A1 | 10/2006 | Goodwin et al. | |
| 2007/0159920 A1 * | 7/2007 | Baumfalk et al. | 366/152.4 |
| 2007/0231305 A1 * | 10/2007 | Noll et al. | 435/289.1 |
| 2007/0252290 A1 | 11/2007 | Terentiev et al. | |
| 2007/0292940 A1 * | 12/2007 | Roll | 435/288.7 |
| 2008/0171383 A1 | 7/2008 | Selker et al. | |
| 2008/0234434 A1 * | 9/2008 | Lin et al. | 525/122 |

FOREIGN PATENT DOCUMENTS

| | | |
|---|---|---|
| WO | 9408173 | 4/1994 |
| WO | 2004026702 | 4/2004 |
| WO | 2005108546 | 11/2005 |
| WO | 2011075057 | 6/2011 |

OTHER PUBLICATIONS

Supplementary European Search Report dated Sep. 23, 2013 issued on corresponding EP application No. 10837965.2.

* cited by examiner

SENSOR ATTACHMENT ARRANGEMENT FOR FLEXIBLE BAGS

CROSS-REFERENCE TO RELATED APPLICATIONS

This application is a filing under 35 U.S.C. 371 of international application number PCT/SE2010/050668, filed Jun. 15, 2010, published on Jun. 23, 2011 as WO 2011/075036, which claims priority to application number 0950977-9 filed in Sweden on Dec. 17, 2009.

TECHNICAL FIELD OF THE INVENTION

The present invention relates to an optical sensor holding device.

BACKGROUND OF THE INVENTION

Bioreactors are used in the bioprocess industry for growing cells, e.g. for the purpose of producing biopharmaceuticals. Disposable bioreactors have been used more and more and are an increasing trend in the industry. These disposable bioreactors are flexible bags made of plastic, for example welded polyethylene film. For the culturing of cells it is important to measure some features of the culture inside the bioreactor. The features could be for example temperature, pH, and dissolved oxygen (DO) etc. In flexible bags it is common to provide sensors from the upper side of the bag, like the Cellbag™ 50 L/pH from GE Healthcare. One disadvantage with this is the risk of the sensor not being inside the culture all the time. Optical sensors for measuring for example pH and DO are provided from for example PreSens. Such an optical sensor, sometimes called a sensor spot, is a spot of a dye material typically comprising two different fluorescent materials. When the sensor spot is illuminated, fluorescent substances of the spot will emit light. Using suitable fluorescent substances this emitted light can be indicative of a property of the culture, such as pH or DO. Thus the returned light can be analysed and for example pH or DO can be determined. For optimal performance, these sensors should be provided in the culture all the time. Providing the sensors in the bottom part of the bag is often not as convenient as providing the sensor from the upper side due to the support structure often provided under the bag. Furthermore these optical sensors typically can not be attached directly on the material of the bag due to chemical incompatibility. Another issue is that the sensor assembly should be as flat as possible to ensure that it always will remain under the liquid surface.

SUMMARY

It is an object of the present invention to provide an optical sensor holding device that solves the problems of prior art described above.

This is achieved in an optical sensor holding device according to claim 1.

Suitable embodiments are described in the dependent claims and in the detailed description below.

BRIEF DESCRIPTION OF THE DRAWINGS

FIG. 1b is an exploded view of the system shown in FIG. 1a.

FIG. 7b is an exploded view of the inner and outer sensor holding parts of FIG. 7a.

DETAILED DESCRIPTION OF THE EMBODIMENTS

Figure 1A:
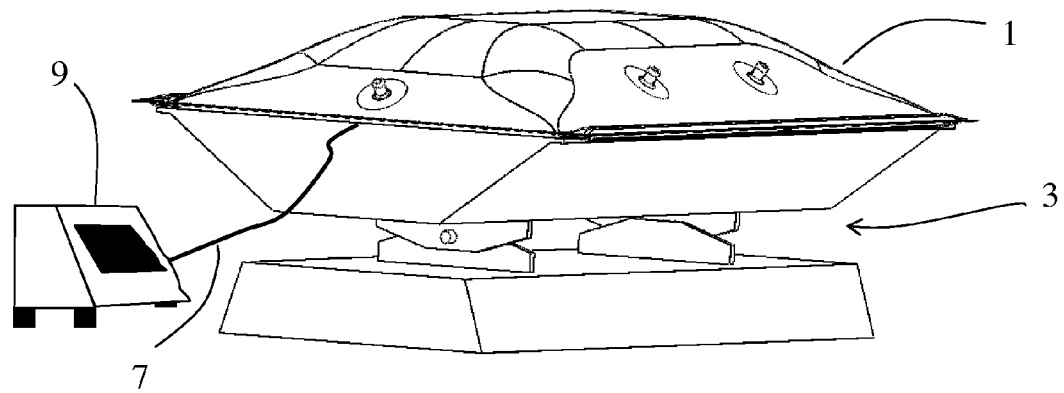
FIG. 1a is a schematic view of a bioreactor in a rocking support structure provided with an optical sensor according to the invention.
Figure 1B:
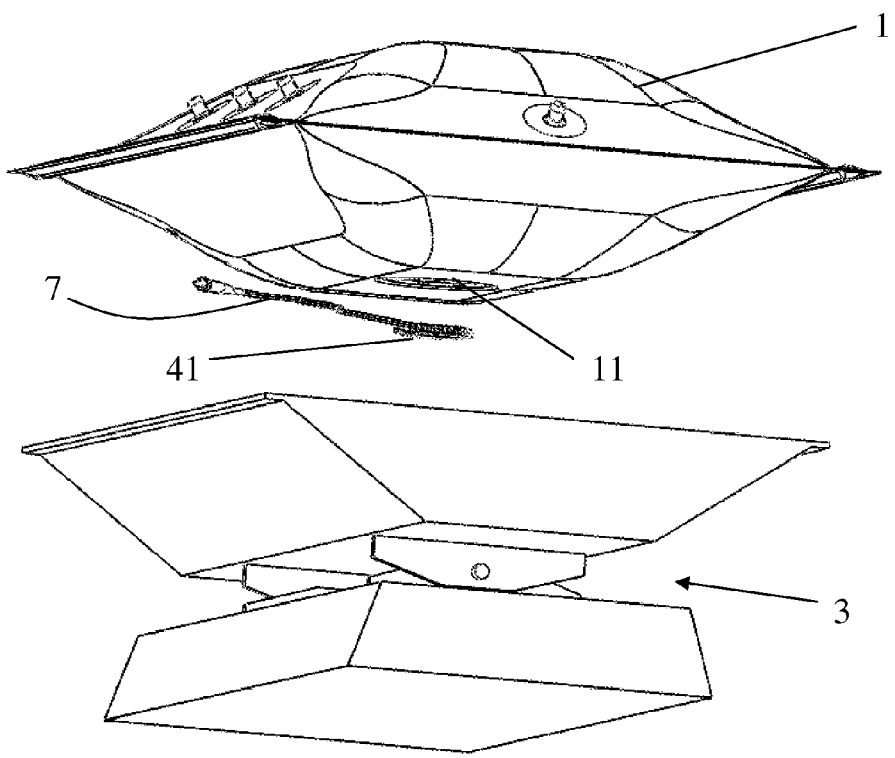

FIG. 1a is a schematic view of a bioreactor 1 in a rocking support structure 3. FIG. 1b shows the same bioreactor system but in an exploded view. In the bottom part of the bioreactor 1 a sensor holding part 11 is provided according to the invention. The sensor holding part holds an optical sensor on the inside of the bag. Details of this will be described further down in the description. An optical fibre 7 is provided to a position close to the position of the optical sensor but outside the bag with the help of an adaptor part 41 (described in detail below). A monitor 9 is also shown where the readings from the optical sensor can be monitored.

According to the invention a sensor holding part (also called an optical sensor holding device) is provided inside the bag. The sensor holding part is integrated with the bag by means of for example welding. An adaptor part holding the optical fibre is provided outside the bag. The sensor holding part comprises an optical sensor and first locking parts protruding out from the bag. These first locking parts are adapted to mate with second locking parts of the adaptor part such that the optical fibre in the adaptor part will be safely positioned to and can communicate with the sensor inside the bag. Suitably the locking parts provide a locking mechanism that holds the optical fibre in a stable position in relation to the sensor in all directions. Suitably the optical fibre is provided lying flat along the bottom of the bag, i.e. the optical fibre is not pointing towards the sensor in the bag. Instead a mirror is provided in the adaptor part such that the light can be directed to the sensor when the adaptor part is positioned below the sensor. This is suitable because the support structure does not need to be adapted to the sensor attachment arrangement. Hereby this sensor attachment arrangement can be used on already existing systems without any adaptation. Furthermore, since no part of the sensor attachment arrangement is secured to the support structure, the bag can be freely moved together with the sensor and the sensor attachment arrangement. More description around the details of suitable embodiments of the invention is given below.

Figure 2A:
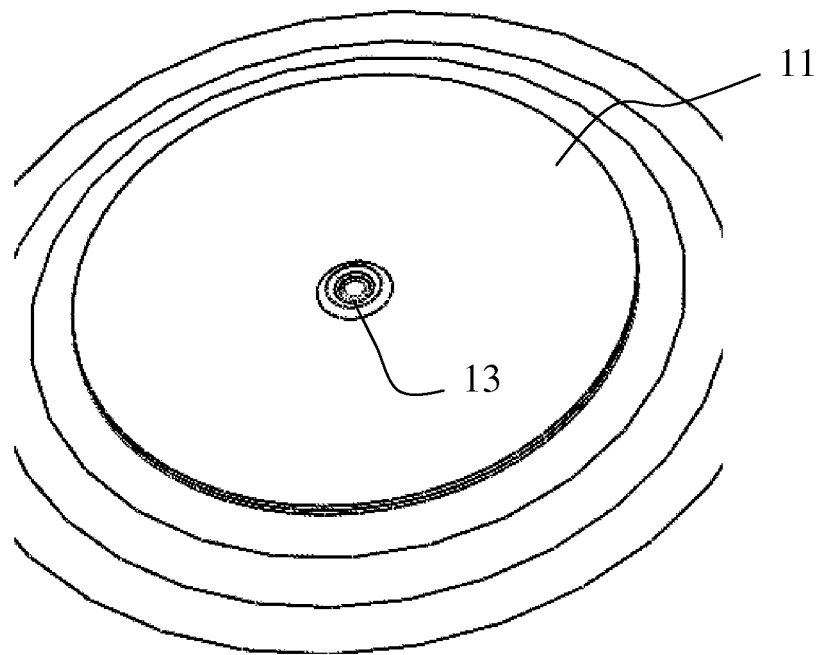
FIG. 2a shows a sensor holding part according to one embodiment of the invention from one side.

FIG. 2a is a view of a sensor holding part 11 (also called an optical sensor holding device 11) according to one embodiment of the invention. The sensor holding part 11 is in one embodiment positioned inside the bag and secured to the inner bag surface for example by means of welding. In another embodiment the sensor holding part is welded to the outside of the bag surface and a hole is provided in the bag surface around the sensor. In FIG. 2a the side adapted to face the interior of the bag is shown. In this embodiment the sensor holding part 11 is circular. This is suitable because a circular shape will give rise to less tension in the joint between the bag and the sensor holding part than would a shape with sharp edges. Furthermore, tension stress can cause creeping deformation of the sensor holding part. The circular geometry also reduces the risk for dimension changes due to different shrinkage in the molding process. However other geometries of the sensor holding part would also be possible. In the centre of the sensor holding part 11 the optical sensor 13, is provided. The optical sensor is a dye as described in the background chapter and can also be called a sensor spot. The sensor holding part should be provided in a material that can be welded to the bag material. The bag is often made from polyethylene and in this embodiment also the sensor holding part is made from polyethylene. However, the material of the sensor 13 can not be attached directly to polyethylene and therefore the sensor has been provided on a small piece of another material to which the sensor can be attached and which is transparent. In this embodiment polycarbonate has been used. This is described in more detail below in relation to FIG. 3.

Figure 2B:
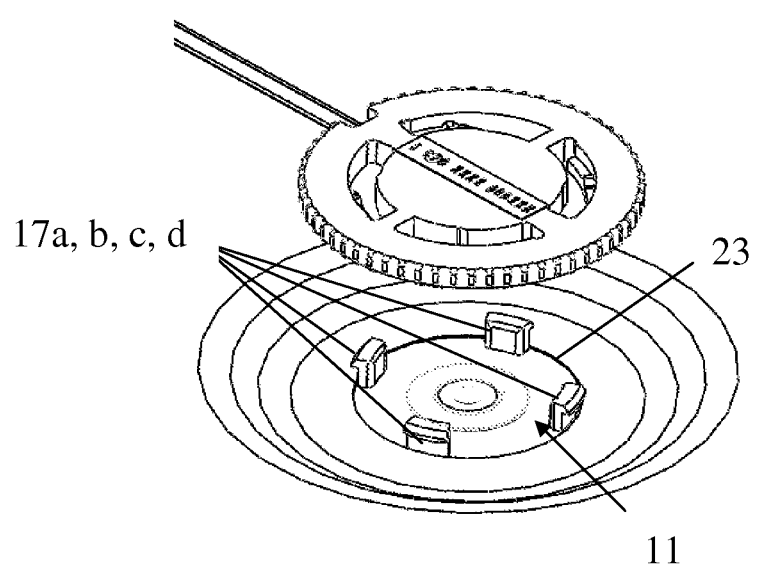
FIG. 2b shows the sensor holding part of FIG. 2a from the other side.

FIG. 2b shows the sensor holding part 11 of FIG. 2a from the other side, i.e. from the side pointing out from the bag. In this embodiment four first locking means in the form of hooks 17a, 17b, 17c, 17d are provided protruding out from the sensor holding part. The hooks are provided on the circumference of a circle. The number of the hooks can also be 2, 3, 5 or even more. The first locking means 17a, b, c, d are adapted to protrude out from the bag when the sensor holding part is positioned inside the bag. At least one hole needs to be provided in the bag surface to let the first locking means 17 a, b, c, d through. In one embodiment a circular hole 23 as large as comprising all the first locking means 17a, b, c, d is provided in the bag. The sensor holding part is welded to the bag in order to prevent any leakage. In another embodiment the same circular hole is provided in the bag and furthermore a smaller circular piece of bag film is welded over the central part of the sensor holding part but inside the first locking means 17 a, b, c, d. This smaller circular piece of bag film will hereby cover the sensor in the middle of the sensor holding part. This could be suitable if there is any risk of leakage through the sensor attaching arrangement. This is described in more detail below in relation to FIG. 3. In another embodiment it would also be possible to provide one separate hole in the bag for each first locking means, i.e. in this embodiment four holes would be provided. The sensor holding part needs then to be welded to the bag around all these four holes in order to prevent any leakage. Alternatively, the bag surface could be welded to the sensor holding part in one circle on the inside of the locking means and one circle outside the locking means.

Figure 3A:
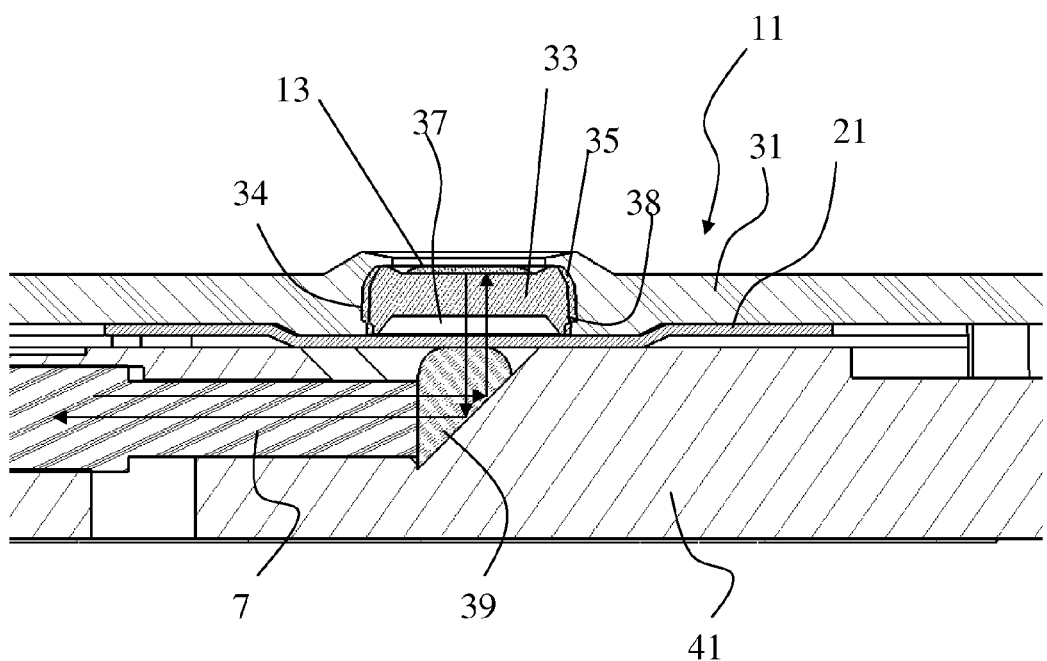
FIG. 3a is a cross section of the sensor attaching arrangement according to one embodiment of the invention.

FIG. 3a is a cross section of a central part of the sensor attachment arrangement according to one embodiment of the invention. According to the invention the sensor holding part 11 (also called the optical sensor holding device 11) comprises two parts. One bag attachment part 31 adapted to be welded to the bag and one sensor attachment part 33 where the sensor 13 is provided. The sensor attachment part 33 is made of a material to which the sensor 13 can be attached. This could be for example polycarbonate. The sensor attachment part 33 is pressed fit into an opening 34 in the bag attachment part 31. The bag attachment part 31 is made from a material that can be welded to the bag. Many bags are made from polyethylene and in this example also the bag attachment part 31 is made from polyethylene. The reason why the sensor 13 is not attached directly to the bag attachment part 31 is that the sensor 13 used in this example can not be attached to a material that also can be welded to the bag. The bag is made from polyethylene and therefore a suitable material for the sensor holding part is polyethylene. However the material of the sensor 13 used in this example can not be attached to polyethylene. The press fit of the sensor attachment part 33 in the opening 34 in the bag attachment part 31 disclosed here in relation to FIG. 3a is a way to solve this problem. The sensor attachment part 33 should be slightly bigger than the opening 34. Furthermore the sensor attachment part 33 is provided with a chamfer 35. This will give a radial pressure on the sensor attachment part 33 for the purpose of preventing leakage through the free press fit. This minimizes the risk of getting any liquid or dirt in the opening 37 below the sensor attachment part 33 where light will pass during the optical reading.

Furthermore, a locking shoulder 38 is provided in the opening 34 in the bag attachment part 31. The locking shoulder 38 should keep the sensor attachment part 33 in place after having been forced to pass said locking shoulder 38 when pressed fitted into the opening 34.

In this embodiment a circular piece of bag film 21 is also provided. This piece of bag film 21 is welded to the bag attachment part 31 around the central part of the bag attachment part 31 where the sensor 13 is provided. The purpose is to prevent any possible leakage outside the bag if such a leakage would occur through the press fit. However, if the press fit really is leakage free and reliable this circular piece of bag film 21 would not be necessary.

In FIG. 3a an adaptor part 41 is also shown attached to the sensor holding part 11. An optical fibre 7 is positioned into the adaptor part 41. A combined mirror and lens 39 is provided in the adaptor part 41 connected to the optical fibre 7. When the sensor holding part 11 and the adaptor part 41 are connected the combined mirror and lens 39 is provided right beneath the sensor in the sensor holding part 11. The combined mirror and lens 39 directs and focuses the light from the optical fibre 7 onto the sensor spot 13. The sensor 13 is hereby illuminated via the fibre 7 and the excited fluorescent sensor 13 emits light that is monitored via the fibre 7. The light paths are shown by arrows. With this arrangement the optical fibre is provided along the surface of the bottom part of the bag and the support structure needs not to be adapted in any way. The first and second locking parts keeping the sensor holding part and the adaptor part together will be further described below.

Figure 3B:
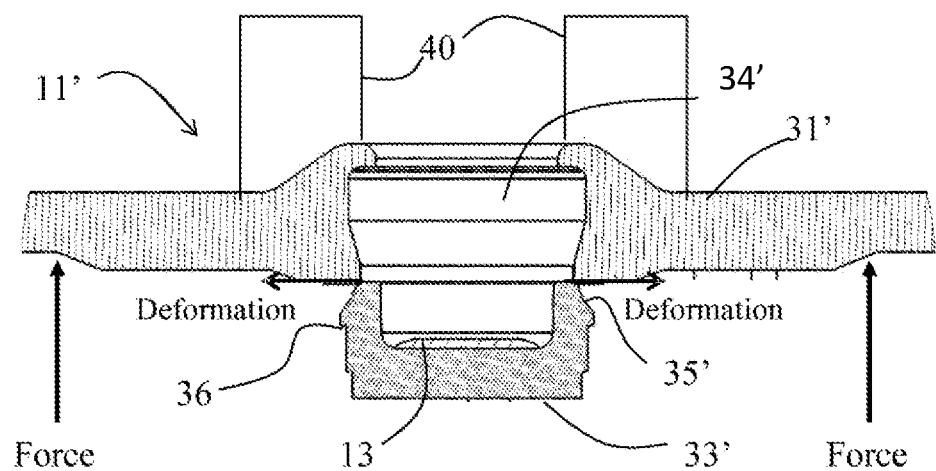
FIG. 3b is a cross section view of another embodiment of the sensor attaching arrangement before assembling.
Figure 3C:
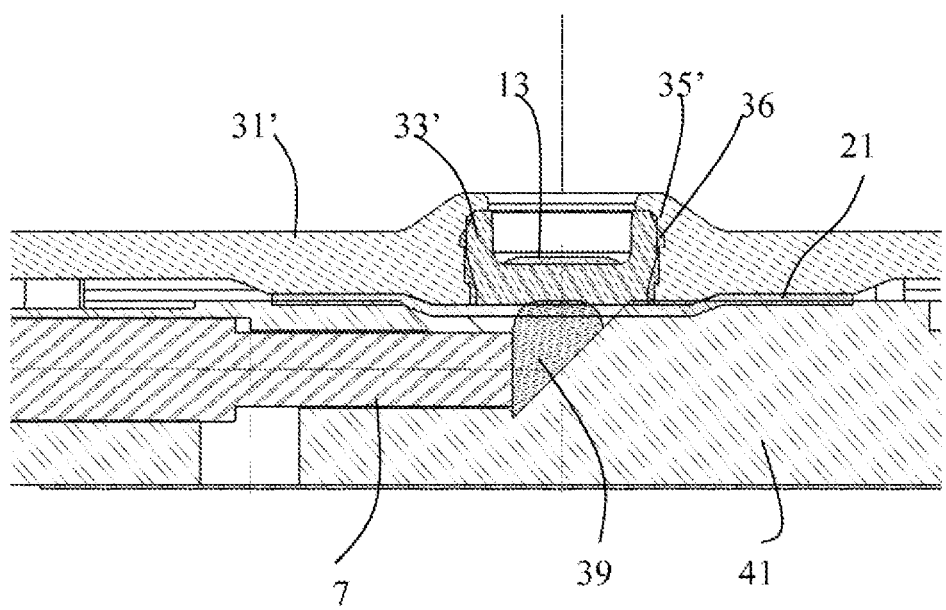
FIG. 3c is a cross section view of the sensor attaching arrangement of FIG. 3b when assembled.

FIG. 3b is a cross section view of a central part of the sensor attachment arrangement according to another embodiment of the invention before assembly. FIG. 3c is a cross section of the embodiment shown in FIG. 3b after assembly. According to the invention a sensor holding part 11' (also called an optical sensor holding device 11') comprises two parts. One bag attachment part 31' adapted to be welded to the bag and one sensor attachment part 33' where the sensor 13 is provided. The sensor attachment part 33' is made of a material to which the sensor 13 can be attached. This could be for example polycarbonate. The sensor attachment part 33' is pressed fit into an opening 34' in the bag attachment part 31'. The bag attachment part 31' is made from a material that can be welded to the bag. Many bags are made from polyethylene and in this example also the bag attachment part 31' is made from polyethylene. The reason why the sensor 13 is not attached directly to the bag attachment part 31' is that the sensor 13 used in this example can not be attached to a material that also can be welded to the bag. The bag is made from polyethylene and therefore a suitable material for the sensor holding part is polyethylene. However the material of the sensor 13 used in this example can not be attached to polyethylene. The press fit of the sensor attachment part 33' in the opening 34' in the bag attachment part 31' disclosed here in relation to FIGS. 3b and 3c is a way to solve this problem. The sensor attachment part 33' should be slightly bigger than the opening 34'. In this embodiment described in FIGS. 3b and 3c suitably a force is applied around the opening 34' combined with a holding device 40 on the opposite side as shown by the force arrows in FIG. 3b when the sensor attachment part 33' should be pressed into the bag attachment part 31'. Hereby the entrance into the opening 34' will get larger (see also deformation arrows) and it will be easier to insert the sensor attachment part 33'. When the sensor attachment part 33' is in place the force will be released and the sensor attachment part 33' will be positioned stably in the opening 34'. Furthermore the sensor attachment part 33' is provided with a chamfer 35'. This will give a radial pressure on the sensor attachment part 33' for the purpose of preventing leakage through the free press fit.

Furthermore, a hook 36 is provided on the sensor attachment part 33' which hook 36 will be pressed into the walls of the opening 34' of the bag attachment part 31' after insertion and assure a stable position of the sensor attachment part 33' in the bag attachment part 31'.

FIG. 3c is a cross section view of the sensor attaching arrangement of FIG. 3b when assembled. In FIG. 3c an adaptor part 41 is also shown attached to the sensor holding part 11'. An optical fibre 7 is positioned into the adaptor part 41. A combined mirror and lens 39 is provided in the adaptor part 41 connected to the optical fibre 7. When the sensor holding part 11' and the adaptor part 41 are connected the combined mirror and lens 39 is provided right beneath the sensor in the sensor holding part 11'. The combined mirror and lens 39 directs and focuses the light from the optical fibre 7 onto the sensor spot 13. The sensor 13 is hereby illuminated via the fibre 7 and the excited fluorescent sensor 13 emits light that is monitored via the fibre 7. The light paths are shown by arrows. With this arrangement the optical fibre is provided along the surface of the bottom part of the bag and the support structure needs not to be adapted in any way. The first and second locking parts keeping the sensor holding part and the adaptor part together will be further described below. In this embodiment a circular piece of bag film 21 is also provided. This piece of bag film 21 is welded to the bag attachment part 31' around the central part of the bag attachment part 31' where the sensor 13 is provided. The purpose is to prevent any possible leakage outside the bag if such a leakage would occur through the press fit. However, if the press fit really is leakage free and reliable this circular piece of bag film 21 would not be necessary.

Figure 4A:
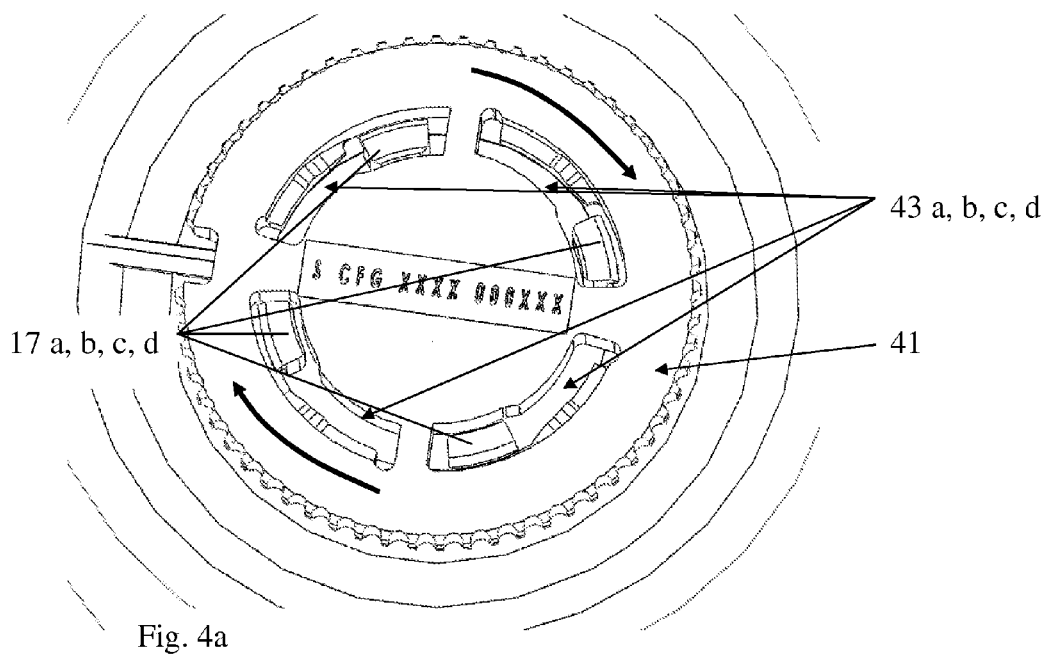
FIG. 4a shows an adaptor part according to one embodiment of the invention in a non locked position.
Figure 4B:
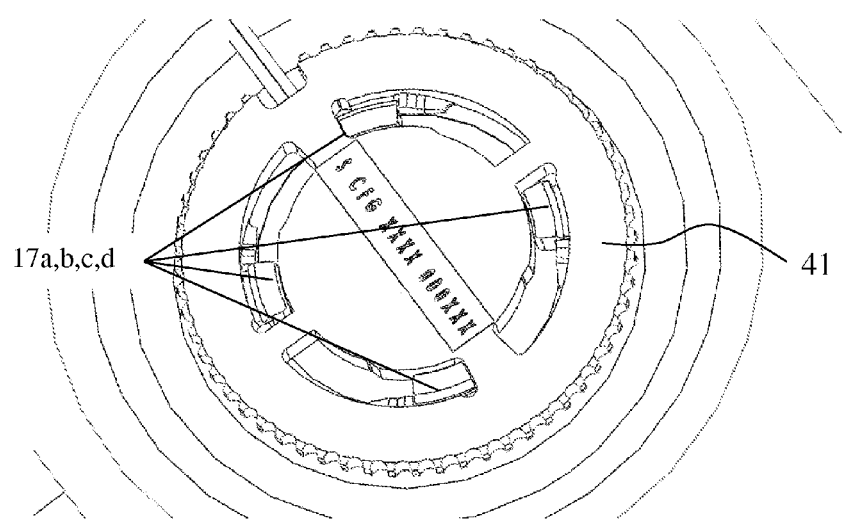
FIG. 4b shows the adaptor part of FIG. 4a in a locked position.

FIG. 4a shows an adaptor part 41 according to one embodiment of the invention. Suitably the adaptor part is provided in a material that is stiffer than the material of the sensor holding part 11. One example of a suitable material for the adaptor part is POM (Polyacetal plastic or Delrin plastic) or Peek (polyetereterketone plastic). In FIG. 4a it is shown how the first locking means 17 *a, b, c, d* of the sensor holding part 11 are fitted into second locking means 43 *a, b, c, d,* in the adaptor part 41 in a non locked position. However, the rest of the sensor holding part 11 is not shown in order to make it clearer. The second locking means 43 *a, b, c, d* are in this embodiment provided as four tracks on the circumference of a circle. The dimensions are adapted for receiving the first locking means 17 *a, b, c, d* of the sensor holding part 11. In this embodiment each track 43 *a, b, c, d* comprises guiding surfaces leading the hooks into a locking position, i.e. after having rotated the adaptor part 41 in relation to the sensor holding part 11 (as shown in FIG. 4b) the first locking means 17 *a, b, c, d* have been guided into a second position within the tracks which is a locked position. These details are described in relation to FIGS. 5a and 5b.

FIG. 4b shows the adaptor part of FIG. 4a in a locked position.

Figure 5A:
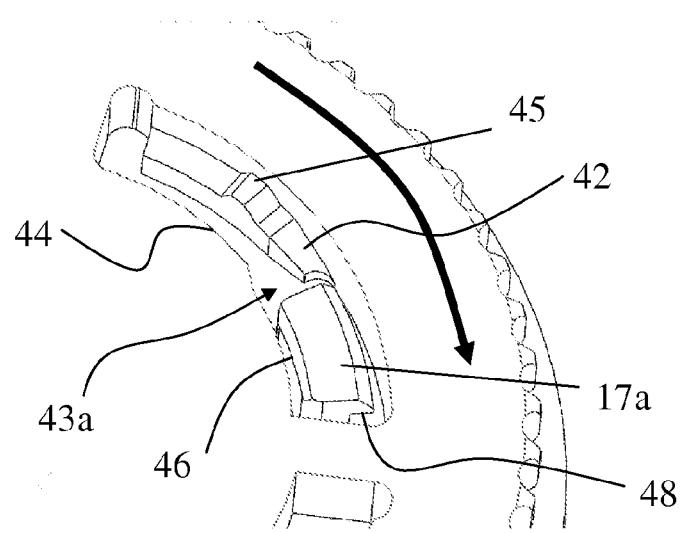
FIG. 5a is a closer view of the locking mechanism in one embodiment of the invention before locking.

FIG. 5a is a closer view of the locking mechanism in one embodiment of the invention before locking. One first locking means 17a in the form of a hook is shown inserted into one second locking means 43a in the form of a track. A radial guiding surface 44 on the inner surface of the track 43a is provided for guiding a corresponding hook guiding surface 46 on the hook 17a into a radial locked position. Possibly the hook 17a is also pressed somewhat outwardly by the guiding surface 44. Furthermore a locking bump 45 is shown in the track 43a. A gripping part 48 of the hook 17a will be caught by an inclined surface 42 of the track leading up to the locking bump 45 and the hook 17a will pass over the locking bump 45 when the adaptor part 41 is rotated in relation to the sensor holding part 11. The purpose of the locking bump 45 is to prevent the hook 17a from rotating back.

Figure 5B:
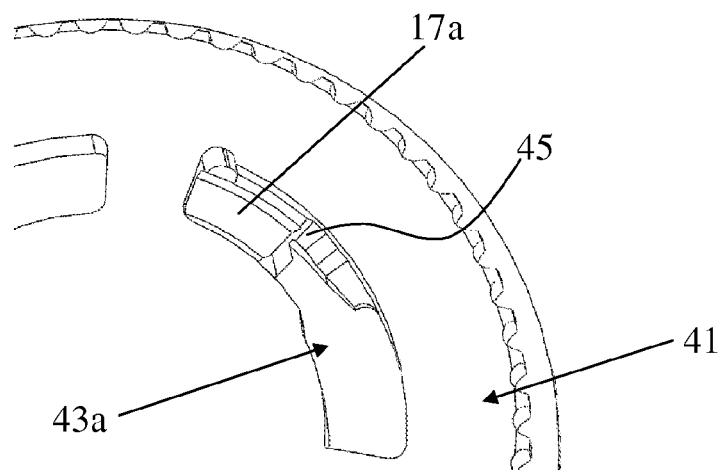
FIG. 5b is the same view as FIG. 5a but in locked position, i.e. the adaptor part has been turned to a locked position.

FIG. 5b is the same view as FIG. 5a but in locked position, i.e. the adaptor part has been rotated to a locked position. Because all four locking parts provided in a circle are locked and because the locking mechanism is securing the adaptor part 41 in relation to the sensor holding part 11 in all directions the combined mirror and lens 39 of the adaptor part 41 can be kept steadily in relation to the sensor 13. Furthermore, this locking mechanism provides a very low tension stress on the sensor holding part. This is important because the sensor holding part is made from polyethylene and this material tends to be subjected to creepings/relaxation. Hereby the risk for creeping/relaxation in the sensor holding part is reduced to a minimum by the locking mechanism described here.

Figure 6:
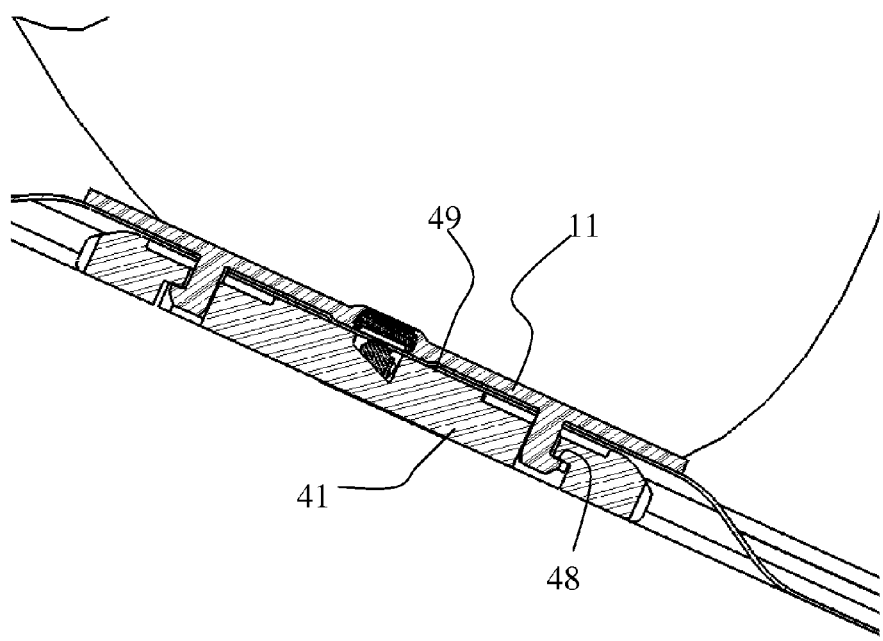
FIG. 6 is a cross section view showing the sensor holding part being locked in the adaptor part according to one embodiment of the invention.

FIG. 6 is a cross section view showing the sensor holding part 11 being locked in the adaptor part 41 according to one embodiment of the invention. In this view a contact surface 49 between the sensor holding part (possibly through the piece of bag film 21) and the adaptor part 41 can be seen. When the gripping part 48 of the hook 17 is pressed by the track 43 into the locked position the sensor holding part and the adaptor part will come into contact at contact surface 49 (possibly through the piece of bag film 21). This contact is important because the distance between the sensor and the combined mirror and lens need to be kept constant and contact surfaces pressed towards each other. This will work well if the tension stress is kept at a minimum level and therefore reduces the risk for creeping of the sensor part.

Figure 7A:
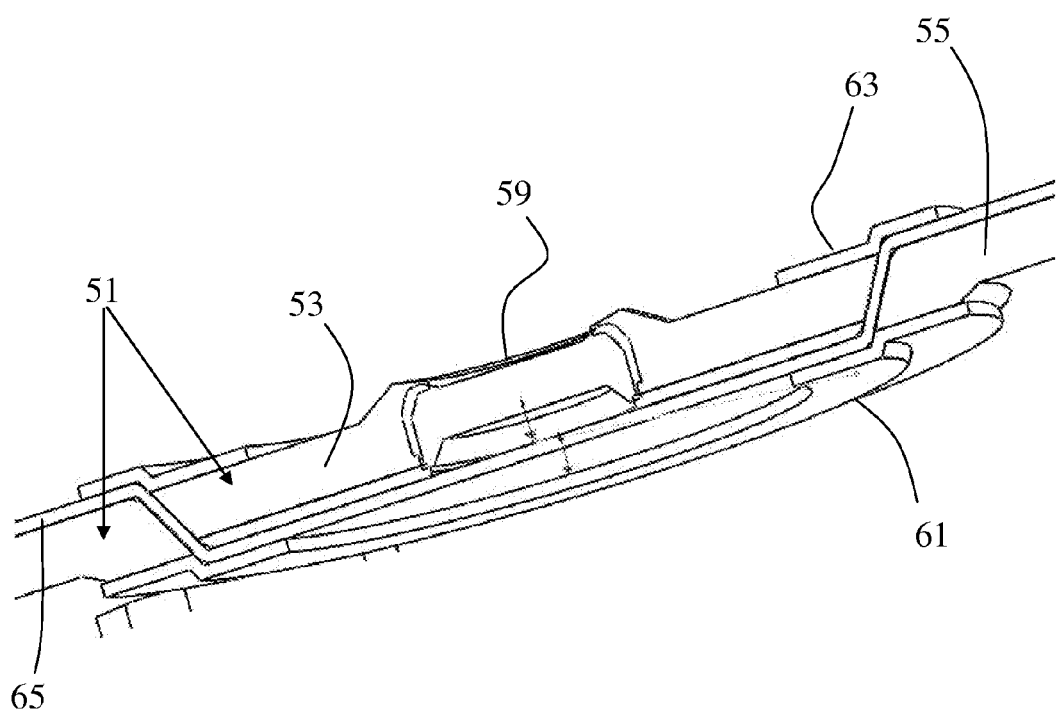
FIG. 7a shows another embodiment of the sensor holding part where the sensor holding part is separated into an inner sensor holding part and an outer sensor holding part.
Figure 7B:
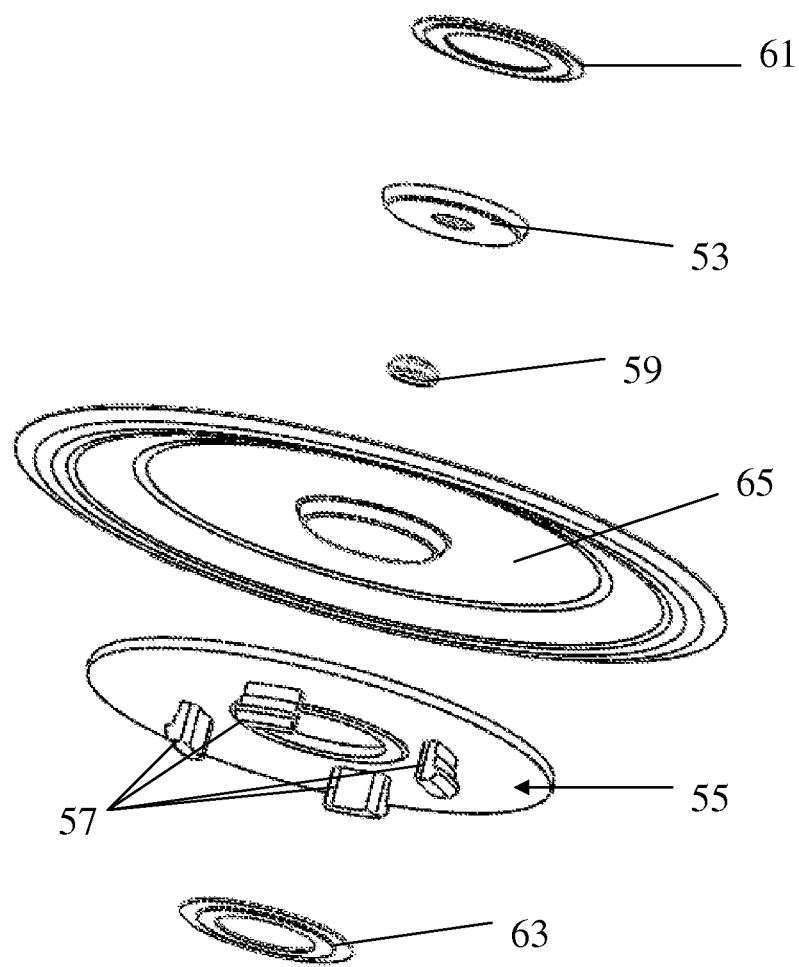

FIG. 7a shows another embodiment of a sensor holding part 51 where the sensor holding part is separated into an inner sensor holding part 53 and an outer locking part 55. FIG. 7b is an exploded view of the sensor holding part of FIG. 7a. In this embodiment the bag 65 needs not to be penetrated by the first locking means. The bioreactor bag surface can be kept intact. This could be good for preventing any contamination risk for the cell growth process. First locking means 57 are provided on the outer locking part 55. The inner sensor holding part 53 is welded to the bag surface and it comprises the sensor 59 in the middle facing the interior of the bag. The sensor attachment arrangement is suitably the same as described in relation to FIG. 3. The outer sensor holding part 55 is welded to the outside of the bag. The inner sensor holding part 53 and the outer locking part 55 will be welded together by bending the bag 65 according to FIG. 7a and then an inner bag support ring 61 and an outer bag support ring 63 will be welded on top and on the bottom and secure the assembly. The adaptor part is suitably the same as described in relation to FIGS. 4a and 4b.

Figure 8A:
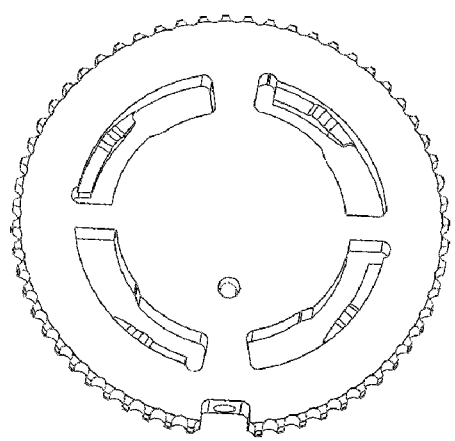
FIGS. 8a-8d shows three different embodiments of adaptor parts according to the invention.
Figure 8B:
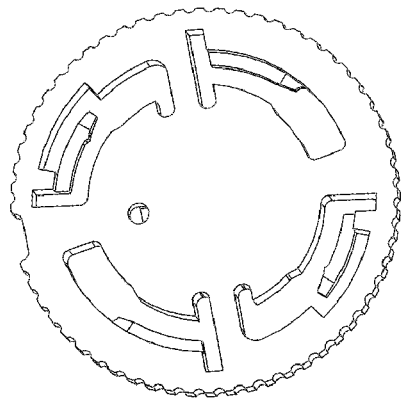
Figure 8C:
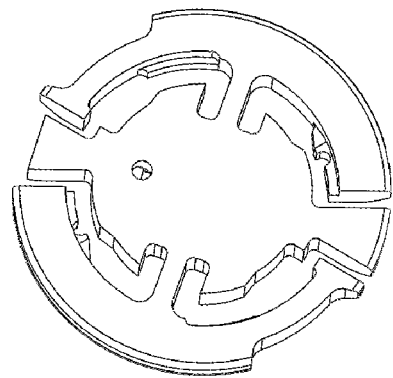
Figure 8D:
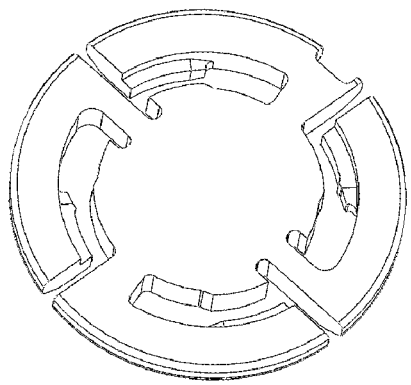

FIGS. 8a-8d shows four different embodiments of adaptor parts according to the invention. Of course both the first and second locking means of the invention can be designed in different forms. The result that should be achieved is a locking position where the two parts are kept together and are locked together in all directions. Furthermore the geometry of the locking is important such that any creeping in the sensor holding part can be prevented. Four alternative embodiments of the adaptor part are shown in FIGS. 8a-8d where FIG. 8a shows the adaptor part already described in relation to FIGS. 4 and 5. In this embodiment the locking is made in axial direction. The embodiments shown in FIGS. 8b, 8c and 8d provide a locking in radial direction.

The sensors described above are optical sensors. These could be for example sensors for pH, DO, carbondioxide ($CO_2$), biomass, UV detection and IR detection.

Figure 9A:
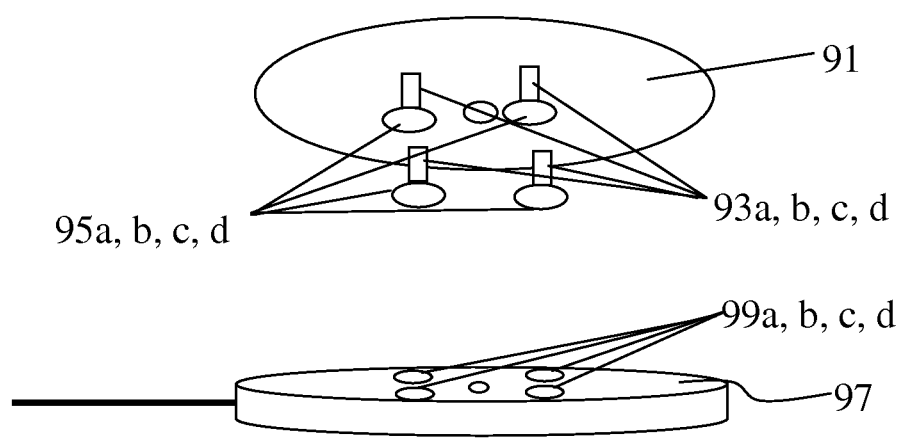
FIGS. 9a and 9b show schematically a sensor holding part and an adaptor part according to another embodiment of the invention.
Figure 9B:
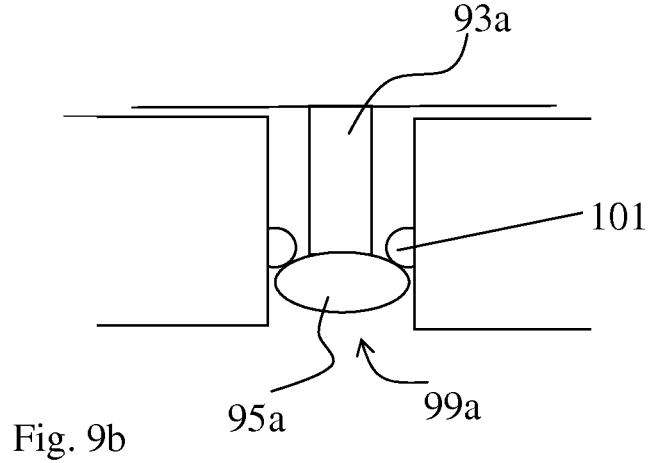

FIGS. 9a and 9b show schematically another embodiment of the invention where the first and second locking parts are designed differently. A sensor holding part 91 is shown having four first locking means 93a, b, c, d in the form of plugs with larger heads 95a, b, c, d. An adaptor part 97 is also shown having four second locking means 99a, b, c, d in the form of receiving holes. In FIG. 9b one of the second locking means 99a is shown in cross section. The second locking means 99a comprises a retaining means 101a in the form of a section in the receiving hole having a smaller diameter than the rest of the hole and edges adapted for letting the larger head 95a of the first locking means 93a pass through the retaining means 101a when a force is applied from above. The edges of the retaining means 101 are further adapted for retaining the head 95a below the retaining means 101 when it has been pressed down there. A sensor is provided in the middle of the sensor holding part in the same way as described in for example relation to FIGS. 2a and b and an optical fibre is provided in the adaptor part in the same way as described in relation to FIG. 3. There are of course many other possible ways of designing the first and second locking means.

One important benefit with the invention is that a support structure provided under the flexible bag need not be adapted in any way to the sensor attachment arrangement. The bag can be freely moved together with the sensor attachment arrangement and be used in any system. Another feature of the sensor attachment arrangement is that it is very flat and of low height. This is advantageous since it is important that its effect on the mixing of the culture in the bioreactor bag by protruding into the bag is limited. At the same time also small volumes of culture in the bag will cover the sensor. The different locking mechanisms described above and the mirror provided in the adaptor part are both important components in making the sensor attachment arrangement as flat as possible.

The invention claimed is:

1. An optical sensor holding device adapted to be integrated with a flexible bag, said device comprising
a bag attachment part made from a same material as that of the flexible bag, and welded to the outside of a bottom surface of the flexible bag and comprising a first opening;
a sensor attachment part made from a transparent material different from that of the bag attachment part and the flexible bag, to which an optical sensor spot can be attached, wherein (i) the sensor attachment part comprises at least one chamfer and is free press fit into the first opening in the bag attachment part that is slightly smaller than the sensor attachment part, and (ii) the at least one chamfer supplies a radial pressure on the sensor attachment part; and
a second opening in the bag attachment part, beneath the sensor attachment part, and above the bottom surface of the flexible bag through which light passes to the sensor attachment part for optical reading.

2. The optical sensor holding device of claim 1, wherein said sensor attachment part is adapted to provide the optical sensor inside the flexible bag in direct communication with a culture liquid inside the bag.

3. The optical sensor holding device of claim 1, wherein the bag attachment part is made from polyethylene and the sensor attachment part is made from polycarbonate.

4. The optical sensor holding device of claim 1, wherein a locking shoulder is provided in the first opening in the bag attachment part whereby the locking shoulder should keep the sensor attachment part in place after having been forced to pass said locking shoulder when pressed fitted into the first opening.

5. The optical sensor holding device of claim 1, wherein the sensor holding device is integrated with the flexible bag in the bottom of the bag.

6. The optical sensor holding device of claim 1, wherein the flexible bag is a bioreactor provided on a support structure.

7. The optical sensor holding device of claim 1, further comprising a bag film combined with a central part of the bag attachment part where the optical sensor part is disposed, wherein the second opening beneath the bag attachment part and the sensor attachment part is formed between the bag film and the sensor attachment part.

8. An optical sensor holding device integrated with a flexible bag, the device comprising
a bag attachment part made from a same material as that of the flexible bag, and welded to the outside of a bottom surface of the flexible bag and comprising a first opening;
a sensor attachment part directly connected with the bag attachment part, and made from a transparent material different from that of the bag attachment part and the flexible bag, and housing an optical sensor spot thereon, wherein (i) the optical sensor spot is indirectly connected with the flexible bag via the sensor attachment part in connection with the bag attachment part, and (ii) the sensor attachment part is free press fit into the first opening in the bag attachment part that is slightly smaller than the sensor attachment part;
a second opening in the bag attachment part, beneath the sensor attachment part, and above the bottom surface of the flexible bag through which light passes to the sensor attachment part for optical reading.

* * * * *